US012558137B2

(12) United States Patent
Zhang et al.

(10) Patent No.: US 12,558,137 B2
(45) Date of Patent: Feb. 24, 2026

(54) INTRA VERTEBRAL DISTRACTION REDUCER

(71) Applicant: THE FOURTH MEDICAL CENTER OF THE GENERAL HOSPITAL OF THE CHINESE PEOPLE'S LIBERATION ARMY, Beijing (CN)

(72) Inventors: Wei Zhang, Beijing (CN); Zhongyang Liu, Beijing (CN); Jiantao Li, Beijing (CN); Meng Li, Beijing (CN); Rui Ma, Beijing (CN); Peifu Tang, Beijing (CN)

( * ) Notice: Subject to any disclaimer, the term of this patent is extended or adjusted under 35 U.S.C. 154(b) by 642 days.

(21) Appl. No.: 17/907,256

(22) PCT Filed: Sep. 6, 2022

(86) PCT No.: PCT/CN2022/117176
§ 371 (c)(1),
(2) Date: Sep. 23, 2022

(87) PCT Pub. No.: WO2023/245876
PCT Pub. Date: Dec. 28, 2023

(65) Prior Publication Data
US 2024/0216029 A1 Jul. 4, 2024

(30) Foreign Application Priority Data
Jun. 23, 2022 (CN) .......................... 202210719386.6
Jun. 23, 2022 (CN) .......................... 202221587734.0

(51) Int. Cl.
*A61B 17/88* (2006.01)
(52) U.S. Cl.
CPC ................................. *A61B 17/885* (2013.01)

(58) Field of Classification Search
CPC .......... A61B 17/025; A61B 2017/0256; A61B 2017/0268; A61B 2017/681;
(Continued)

(56) References Cited

U.S. PATENT DOCUMENTS 7,785,368 B2 * 8/2010 Schaller ............. A61B 17/7097
623/17.11
8,956,365 B2 * 2/2015 Kaiser .................. A61B 17/025
606/90

(Continued)

FOREIGN PATENT DOCUMENTS

WO WO-2004019756 A2 * 3/2004 ......... A61B 17/8858
WO WO-2023245876 A1 * 12/2023 ......... A61B 17/7064

*Primary Examiner* — Anu Ramana
(74) *Attorney, Agent, or Firm* — Novoclaims Patent Services LLC; Mei Lin Wong

(57) ABSTRACT

Provided is an intravertebral distraction reducer, relating to the field of medical instruments, and including a forceps body including a first forceps arm and a second forceps arm which are hinged. An outer sleeve fixedly connected to a working end of the first forceps arm is provided with an elongated slot into which a working end of the second forceps arm is inserted. An inner rod received in the outer sleeve has one end connected to the working end of the second forceps arm, and the other end extending outside the outer sleeve and provided with a distraction ball. The distraction ball includes a sleeve ring slidably received on the inner rod and located between the outer sleeve and a stop block, distraction pieces fixedly connected between the sleeve ring and the stop block and arranged circumferentially around the inner rod, and the stop block fixedly provided on the inner rod.

16 Claims, 16 Drawing Sheets

(58) Field of Classification Search
CPC ............ A61B 17/7065; A61B 17/7097; A61B
17/8855; A61B 17/8858
See application file for complete search history.

(56) References Cited

U.S. PATENT DOCUMENTS

| | | | | |
|---|---|---|---|---|
| 8,986,311 | B2 * | 3/2015 | Boudreault | ........ A61B 17/3421 |
| | | | | 606/90 |
| 9,033,992 | B2 * | 5/2015 | Boudreault | ....... A61M 25/1027 |
| | | | | 606/90 |
| 9,259,329 | B2 * | 2/2016 | Greenhalgh | .......... A61F 2/4455 |
| 10,219,851 | B1 * | 3/2019 | Messerli | ............ A61B 17/8858 |
| 2005/0124989 | A1 * | 6/2005 | Suddaby | ............... A61F 2/4601 |
| | | | | 606/205 |
| 2007/0162136 | A1 * | 7/2007 | O'Neil | .................. A61F 2/4657 |
| | | | | 623/17.12 |
| 2009/0187080 | A1 * | 7/2009 | Seex | ...................... A61B 17/02 |
| | | | | 600/210 |
| 2011/0224742 | A1 * | 9/2011 | Weisel | .................. A61B 34/73 |
| | | | | 606/86 R |

* cited by examiner

B

21

21

INTRA VERTEBRAL DISTRACTION REDUCER

The present invention claims the priority of the applications, filed by the applicant, with the application date of Jun. 23, 2022 and the application No. CN202210719386.6, and entitled "INTRAVERTEBRAL DISTRACTION REDUCER", and with the application date of Jun. 23, 2022 and the application No. CN202221587734.0, and entitled "INTRAVERTEBRAL DISTRACTION REDUCER", respectively, which are incorporated herein by reference in their entirety.

TECHNICAL FIELD

The present invention relates to a medical instrument, and in particular, to an instrument for treating a lumbar spine fracture.

BACKGROUND

For patients suffered from lumbar spine burst fractures, a fixation and reduction mechanism of a pedicle screw rod system is to reduce a fractured vertebral body through indirect pulling. The periphery of the fractured vertebral body can be effectively reduced under the pulling of the annulus fibrosus of the intervertebral disc. However, the central bony block of the anterior middle column cannot be pulled and reduced, thereby causing central collapse loss, and resulting in insufficient reduction. Moreover, a cavity is formed in the reduced vertebral body, thereby causing insufficiency of anterior support, further long-term height loss of the vertebral body, and even degeneration of the intervertebral discs at adjacent segments. Some patients even have aggravated kyphosis, residual waist and back pain, or even an internal fixation failure.

SUMMARY

The technical problem to be solved by the present invention is to provide an intravertebral distraction reducer, which can distract a collapsed bony block from the inside of a fractured vertebral body, so that the fractured vertebral body is reduced well, and occurrence of long-term complications is reduced.

The intravertebral distraction reducer of the present invention includes a forceps body. The forceps body includes a first forceps arm and a second forceps arm which are hinged to each other. One end of each of the first forceps arm and the second forceps arm is a gripping end, and the other ends of the first forceps arm and the second forceps arm are working ends. An outer sleeve is fixedly connected to the working end of the first forceps arm, and an elongated slot is configured to run through the outer sleeve along a radial direction thereof and is also provided along a length direction of the outer sleeve, and the working end of the second forceps arm is inserted into the elongated slot. When the second forceps arm is rotated relative to the first forceps arm, the working end of the second forceps arm may move close to or away from the working end of the first forceps arm along the elongated slot. An inner rod is received in the outer sleeve, and one end of the inner rod is connected to the working end of the second forceps arm. When the working end of the second forceps arm moves close to or away from the working end of the first forceps arm along the elongated slot, the inner rod slides inside the outer sleeve along a longitudinal direction of the outer sleeve. The other end of the inner rod extends outside the outer sleeve, and the other end of the inner rod is provided with a distraction ball. The distraction ball includes a sleeve ring, distraction pieces, and a stop block. The sleeve ring is slidably received on the inner rod, and the stop block is fixedly provided on the inner rod. The sleeve ring is located between the outer sleeve and the stop block. The plurality of distraction pieces are fixedly connected between the sleeve ring and the stop block, and the plurality of distraction pieces are arranged circumferentially around the inner rod. When the sleeve ring moves close to the stop block, the distraction pieces may be deformed in a protruding manner along a direction away from the inner rod.

According to the intravertebral distraction reducer of the present invention, the working end of the second forceps arm is provided with an elongated opening, and the elongated opening is arranged along a length direction of the second forceps arm. One end of the inner rod is fixedly provided with a sliding rod, and the sliding rod is slidably provided in the elongated opening. When the working end of the second forceps arm moves close to or away from the working end of the first forceps arm along the elongated slot, the sliding rod slides inside the elongated opening.

According to the intravertebral distraction reducer of the present invention, one end of the inner rod is provided with two support plates, and the support plates and the inner rod are integrally formed. The working end of the second forceps arm is located between the two support plates. One end of the sliding rod is fixedly connected to one support plate, and the other end of the sliding rod passes through the elongated opening to be fixedly connected to the other support plate.

According to the intravertebral distraction reducer of the present invention, one end of the inner rod is provided with one support plate, the support plate and the inner rod are integrally formed, and the sliding rod is fixedly provided on the support plate.

According to the intravertebral distraction reducer of the present invention, a depth-limiting sleeve is received on the outer sleeve, a threaded hole is formed in the wall of the depth-limiting sleeve, and a limiting screw is threadedly connected to the threaded hole. The limiting screw is configured to fix a position of the depth-limiting sleeve on the outer sleeve. A scale are arranged on the outer wall of the outer sleeve, the scale are arranged along the length direction of the outer sleeve, and the scale displays a distance from the distraction ball in a distracted state to the depth-limiting sleeve.

According to the intravertebral distraction reducer of the present invention, a first arc-shaped rack is fixedly provided at the gripping end of the first forceps arm, and a second arc-shaped rack is fixedly provided at the gripping end of the second forceps arm. The first arc-shaped rack and the second arc-shaped rack extend along the circumferences of first and second circles having a common center at a hinge connecting the first forceps arm and the second forceps arm, and the first arc-shaped rack and the second arc-shaped rack are meshed with each other.

According to the intravertebral distraction reducer of the present invention, the gripping ends of the first forceps arm and the second forceps arm are each provided with a gripping hole.

According to the intravertebral distraction reducer of the present invention, the first forceps arm and the second forceps arm are hinged, wherein the hinge includes a pin shaft.

According to the intravertebral distraction reducer of the present invention, the elongated slot runs through the central axis of the outer sleeve along a radial direction, and the elongated slot communicates with the cavity of the outer sleeve.

According to the intravertebral distraction reducer of the present invention, both the distraction ball and the inner rod are made of a titanium alloy.

According to the intravertebral distraction reducer of the present invention, when the reducer is used, a channel extending into the inside of the fractured vertebral body is provided in a side surface of the fractured vertebral body, and the forceps body is operated to insert the distraction ball in a contracted state, the other end of the inner rod and one end of the outer sleeve close to the distraction ball to the channel and push same into the inside of the fractured vertebral body. Then, the second forceps arm is rotated relative to the first forceps arm, so that the working end of the second forceps arm moves close to the working end of the first forceps arm along the elongated slot. In this case, the inner rod slides towards the inside of the outer sleeve. That is, the distraction ball provided at the other end of the inner rod moves towards the outer sleeve until the sleeve ring of the distraction ball abuts against the outer sleeve. As the inner rod continues to slide towards the inside of the outer sleeve, the sleeve ring is caused to move close to the stop block, so that the distraction pieces may be deformed in a protruding manner along a direction away from the inner rod, the distraction ball is in a distracted state, and the distraction ball in the distracted state supports the collapsed bony block of the fractured vertebral body. Next, the second forceps arm is rotated reversely relative to the first forceps arm, so that the working end of the second forceps arm moves away from the working end of the first forceps arm along the elongated slot. In this case, the inner rod is fixed on the fractured vertebral body due to the fixation effect of the distraction ball. Therefore, the outer sleeve slides relative to the inner rod and exits the channel of the fractured vertebral body, and after the outer sleeve completely exits the fractured vertebral body, it is only required to cut off the inner rod between the outer sleeve and the fractured vertebral body. Hence, in the present invention, the collapsed bony block may be distracted from the inside of the fractured vertebral body, so that the fractured vertebral body is reduced well, and occurrence of long-term complications is reduced.

The present invention will be further described below with reference to the accompanying drawings.

4

Figure 9:
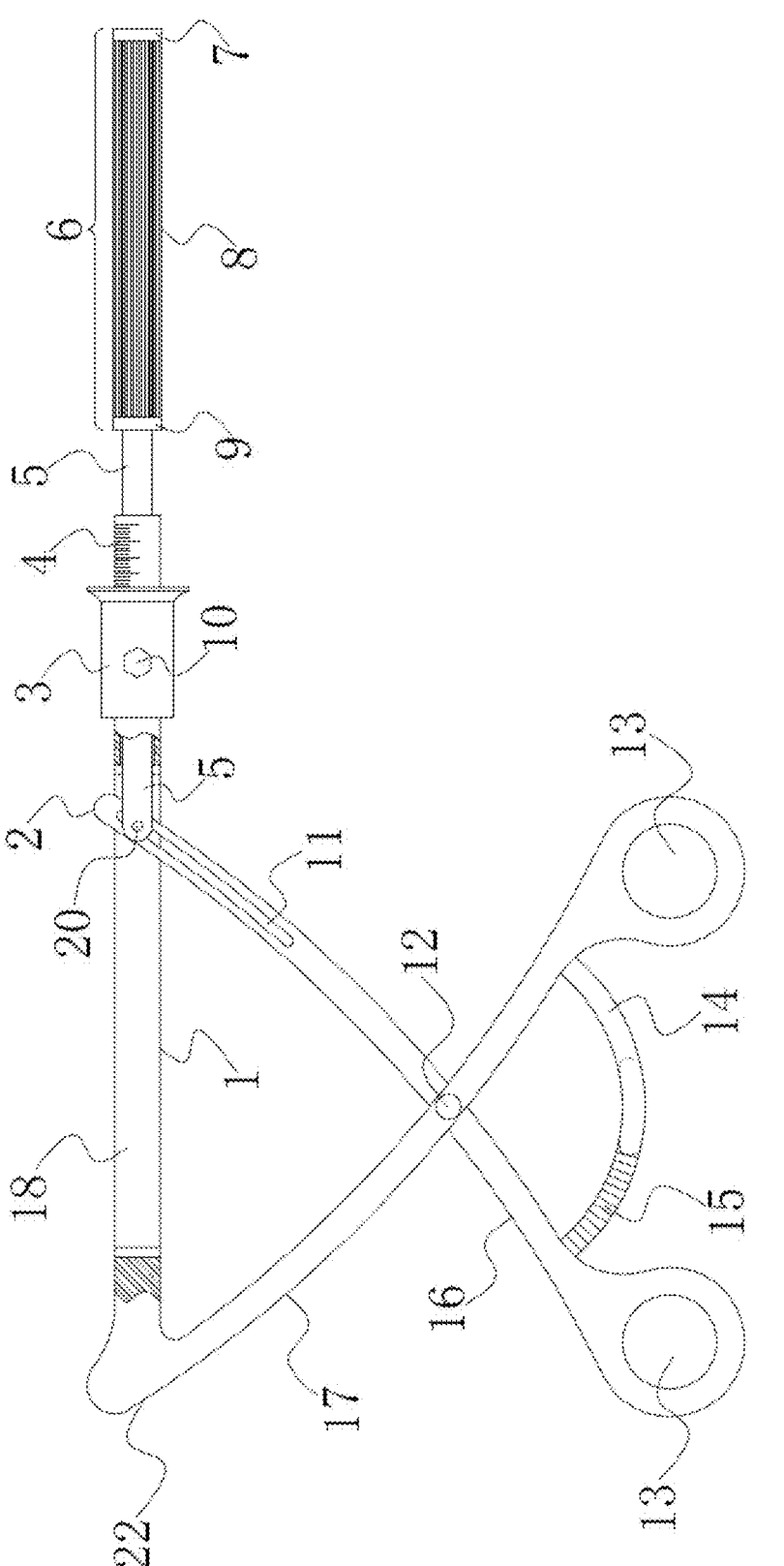
Figure 10:
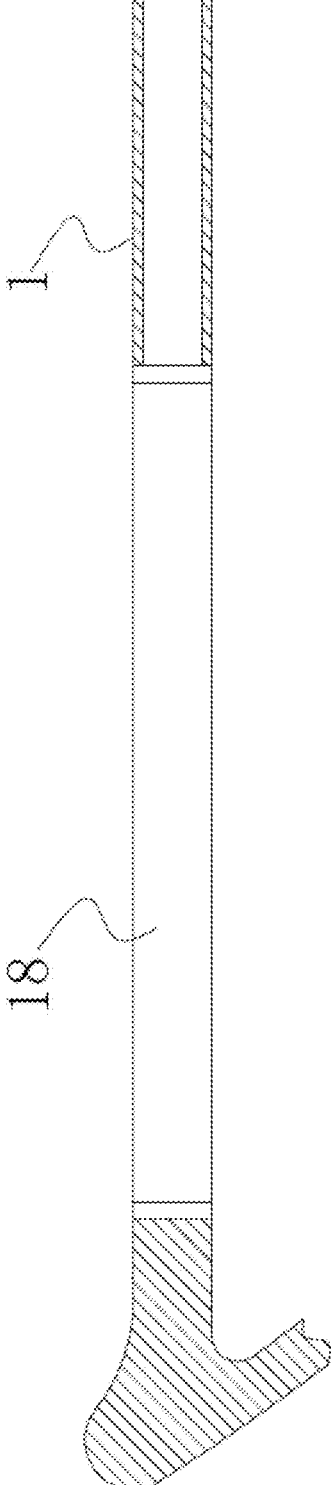
Figure 11:
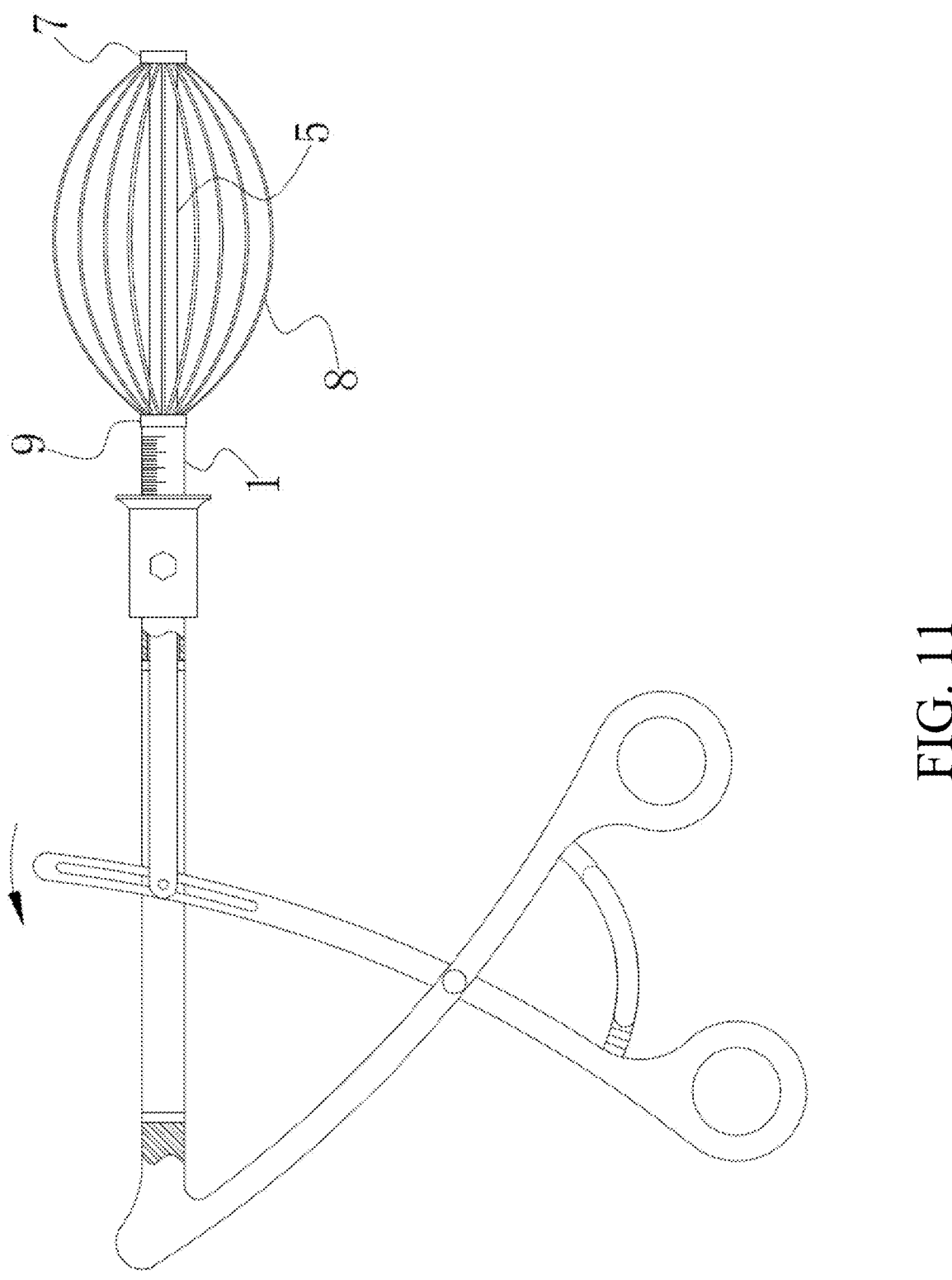
Figure 12:
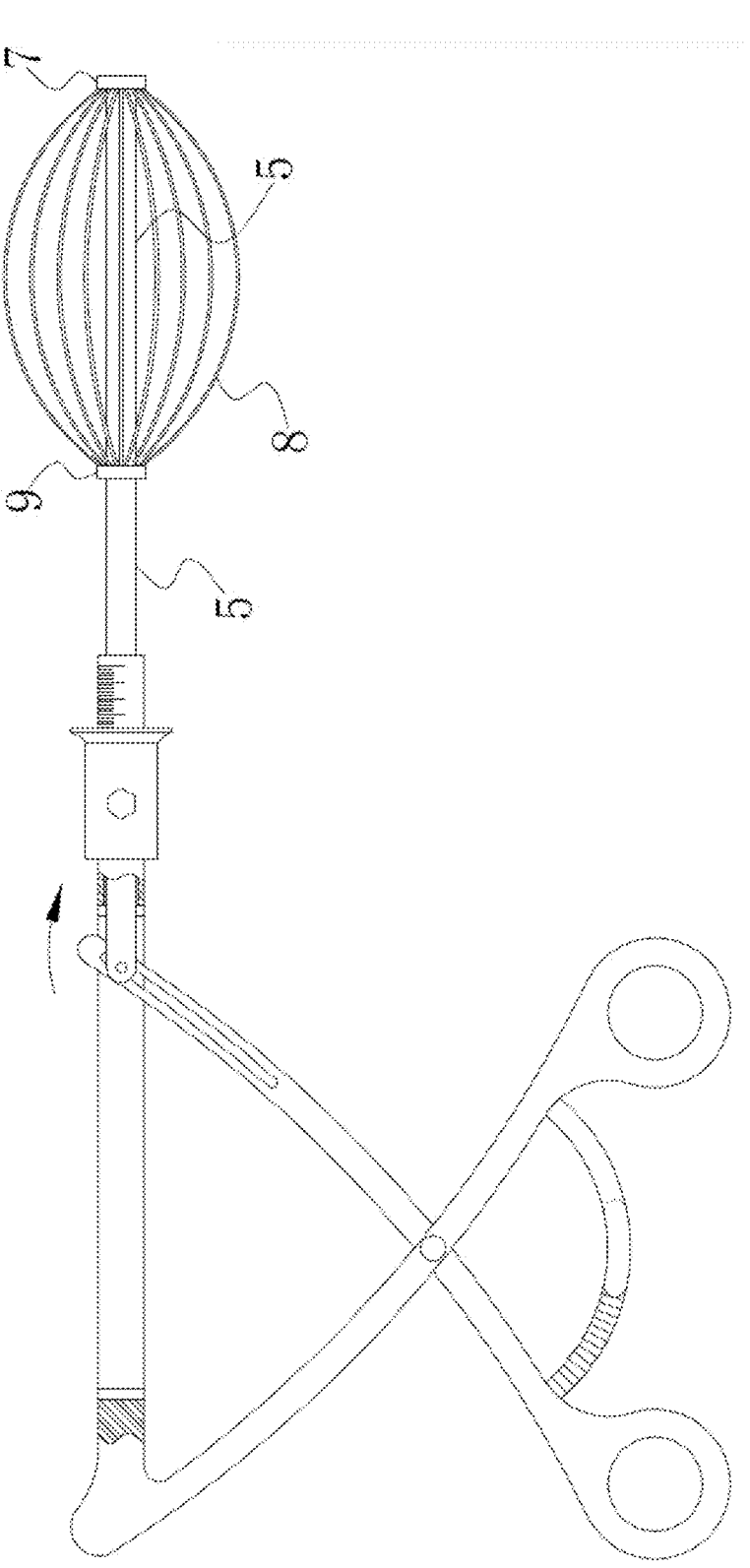
Figure 13:
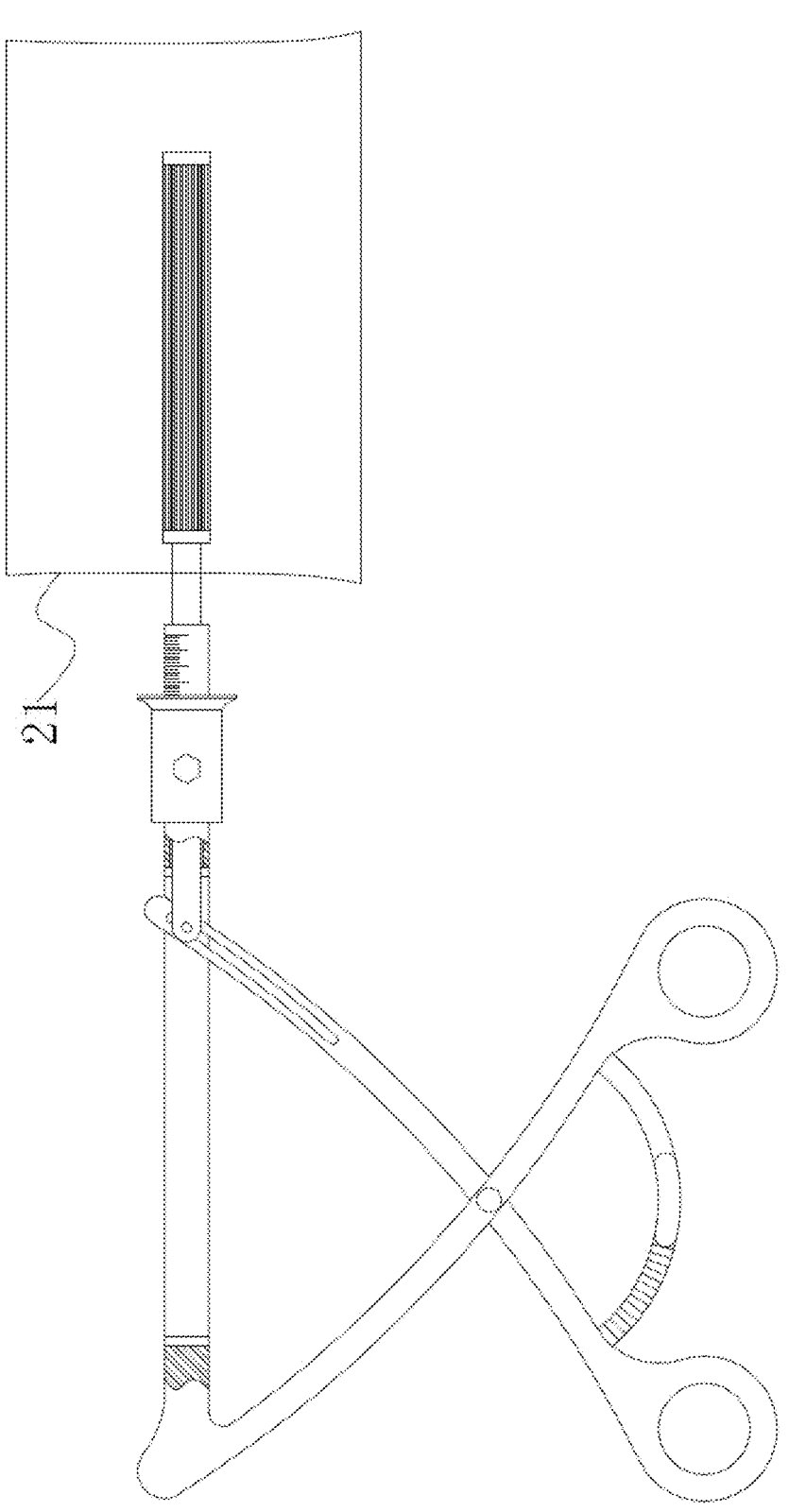
Figure 14:
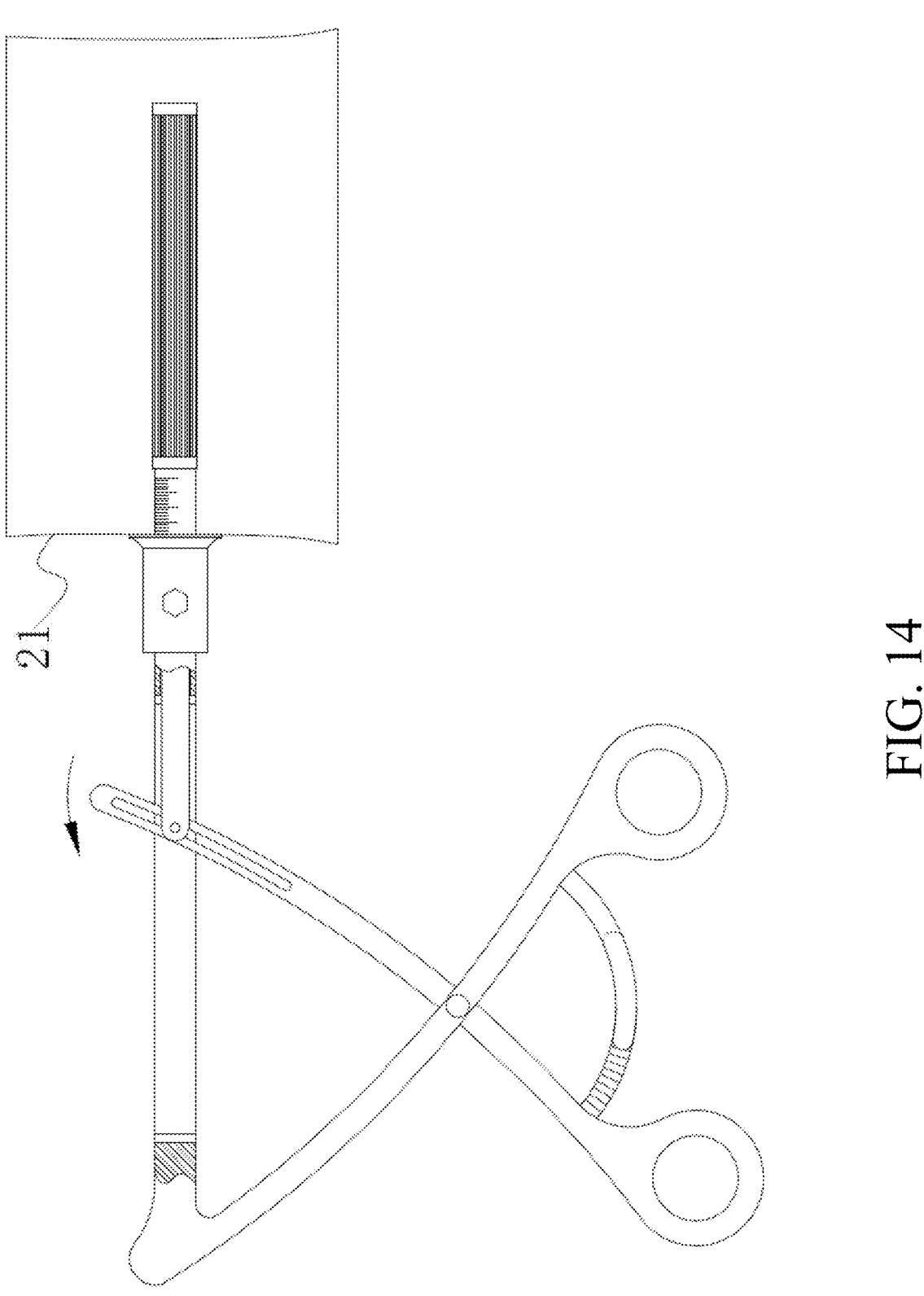
Figure 15:
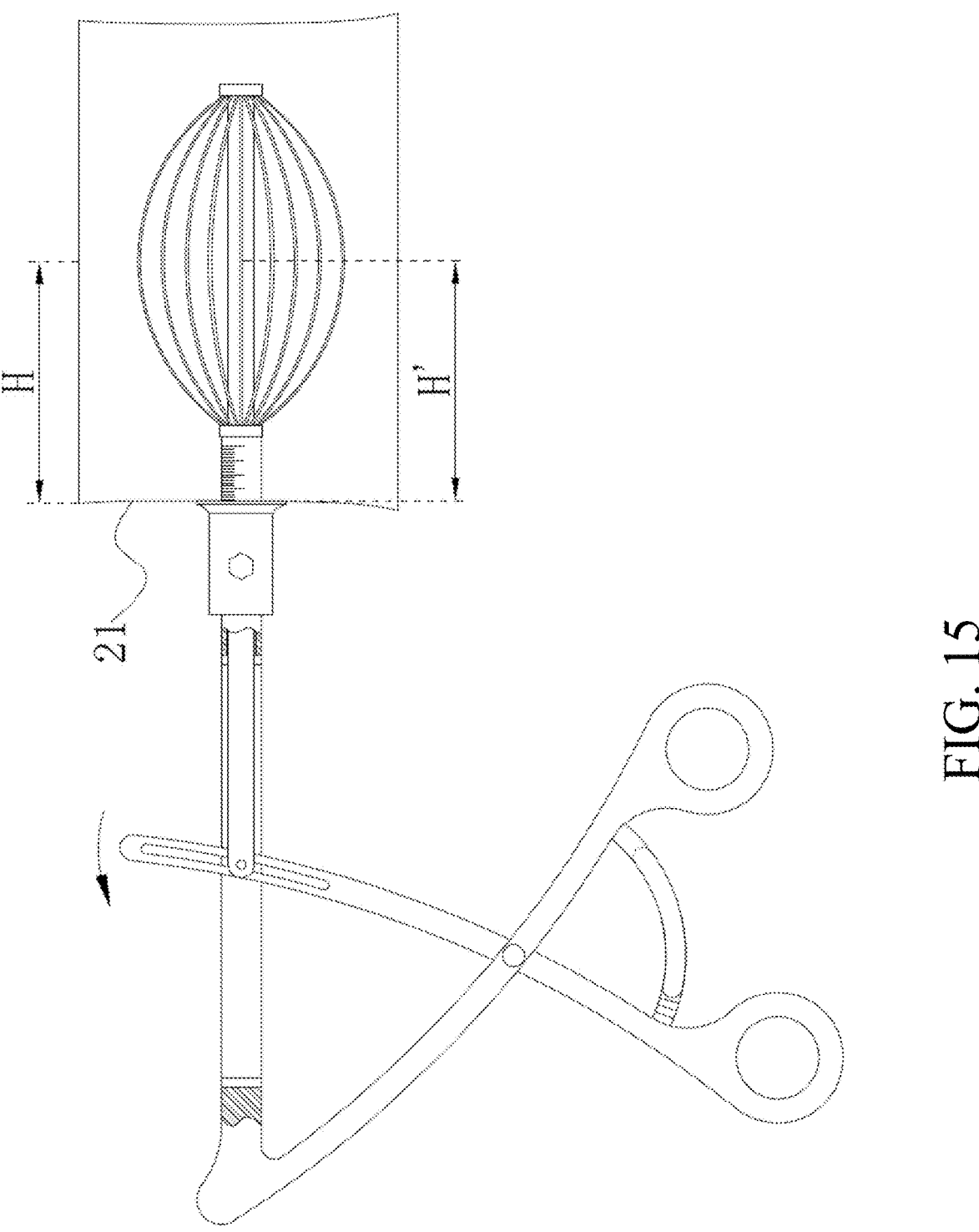
Figure 16:
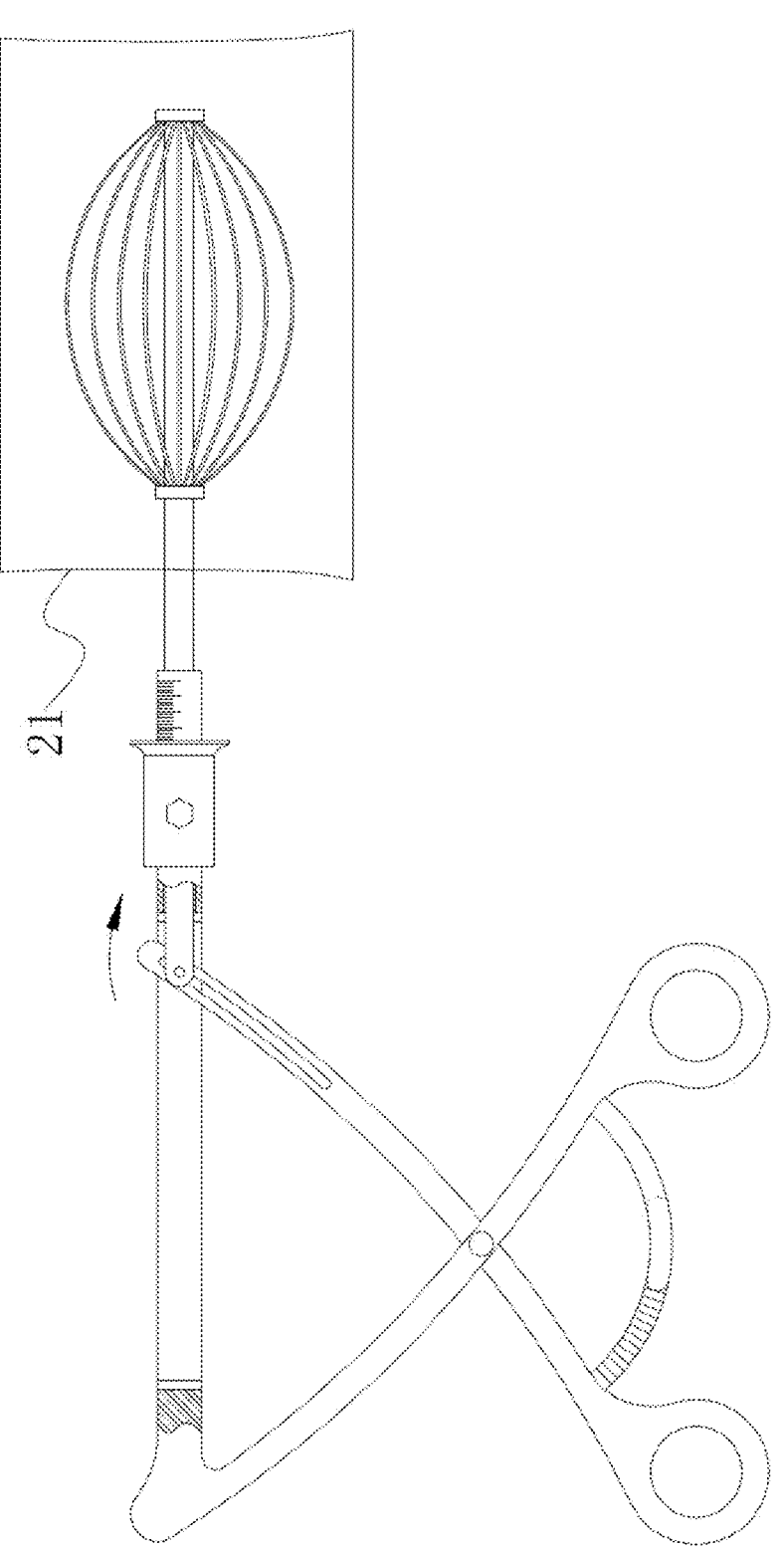

FIG. 9 is a schematic structural diagram of an intravertebral distraction reducer according to the present invention (an outer sleeve is in a cross-sectional state);

FIG. 10 is a cross-sectional view of an outer sleeve according to the present invention;

FIG. 11 is a schematic structural diagram of an intravertebral distraction reducer according to the present invention (a distraction ball is in a distracted state, and a working end of a second forceps arm is close to a working end of a first forceps arm);

FIG. 12 is a schematic structural diagram of an intravertebral distraction reducer according to the present invention (a distraction ball is in a distracted state, and a working end of a second forceps arm is away from a working end of a first forceps arm);

FIG. 13 is a view showing a first use state of an intravertebral distraction reducer according to the present invention;

FIG. 14 is a view showing a second use state of an intravertebral distraction reducer according to the present invention;

FIG. 15 is a view showing a third use state of an intravertebral distraction reducer according to the present invention; and FIG. 16 is a view showing a fourth use state of an intravertebral distraction reducer according to the present invention.

DETAILED DESCRIPTION OF THE INVENTION

To make the foregoing objectives, features and advantages of the present invention more apparent and easier to be understood, specific embodiments of the present invention are illustrated in detail hereinafter in conjunction with the drawings.

The orientations or positional relationships indicated by the terms "upper", "lower", "front", "rear", "left" and "right" appearing in the embodiments of the present invention are based on the orientations or positional relationships shown in the accompanying drawings, are merely intended to facilitate describing the present invention and simplifying the description, rather than indicating or implying that the indicated apparatus must have a specific orientation, and be constructed and operated in a specific orientation, and therefore cannot be understood as a limitation to the present invention.

With respect to the description of the present invention, it should be noted that unless otherwise clearly specified or defined, the terms "provided", "mounted", "connected" and "coupled" should be understood in a broad sense, for example, may be a fixed connection, a detachable connection, or an integral connection; may be a mechanical connection; and may be a direct connection or an indirect connection through an intermediate medium. For persons skilled in the art, the specific meanings of the foregoing terms in the present invention can be understood according to the specific situations.

If the embodiments of the present invention relate to descriptions of "first", "second" and the like, the descriptions of "first", "second" and the like are used for descriptive purposes only and cannot be understood as indicating or implying their relative importance or implicitly indicating the number of indicated technical features.

Figure 1:
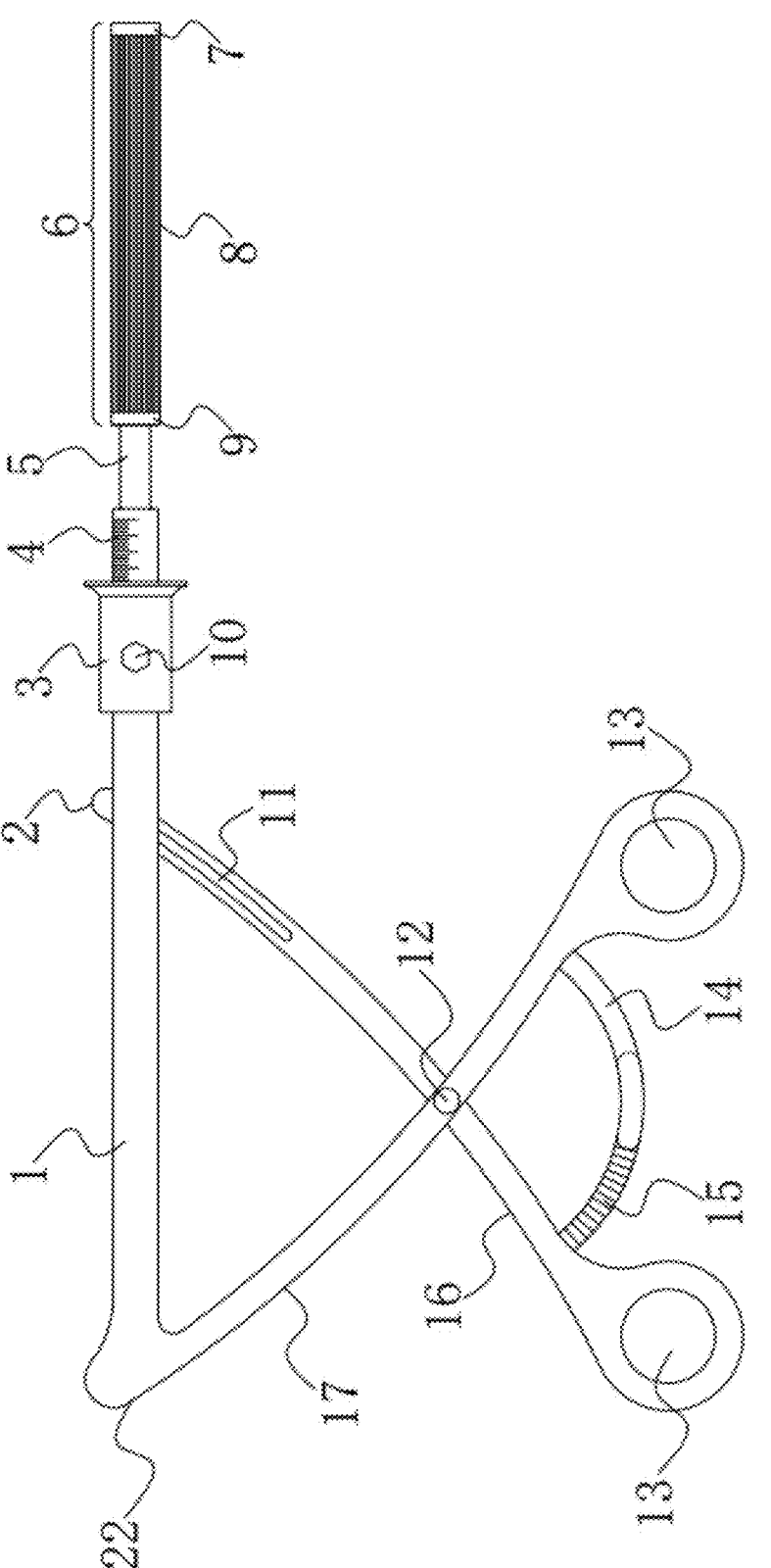
FIG. 1 is a schematic structural diagram of an intravertebral distraction reducer according to the present invention.

As shown in FIG. 1, an intravertebral distraction reducer of the present invention includes a forceps body. The forceps body includes a first forceps arm 17 and a second forceps arm 16 which are hinged to each other. The first forceps arm 17 and the second forceps arm 16 are hinged by a pin shaft 12. The first forceps arm 17 and the second forceps arm 16 hinged to each other are X-shaped. One end of each of the first forceps arm 17 and the second forceps arm 16 is a gripping end, and the other ends of the first forceps arm 17 and the second forceps 16 arm are working ends 22, 2. When a medical worker uses the reducer of the present invention, the medical worker holds the gripping ends of the first forceps arm 17 and the second forceps arm 16 with the hand, so that the gripping ends of the first forceps arm 17 and the second forceps arm 16 are close to or away from each other. Since the two forceps arms are hinged to each other, the working ends 22, 2 of the first forceps arm 17 and the second forceps arm 16 are also close to or away from each other.

As shown in FIG. 1, in combination with FIG. 2 to FIG. 12, an outer sleeve 1 is fixedly connected to the working end 22 of the first forceps arm 17, and an elongated slot 18 is formed on the outer sleeve 1. The elongated slot 18 runs through the outer sleeve 1 along a radial direction and is provided along a length direction of the outer sleeve 1. The feature that the elongated slot 18 runs through the outer sleeve 1 means that the elongated slot 18 extends from the outer wall on one side of the outer sleeve 1 to the outer wall on the other side of the outer sleeve 1 along a radial direction. The elongated slot 18 runs through the central axis of the outer sleeve 1 along a radial direction, and the elongated slot 18 communicates with the cavity of the outer sleeve 1. The working end 2 of the second forceps arm 16 is inserted into the elongated slot 18. When the second forceps arm 16 is rotated relative to the first forceps arm 17, the working end 2 of the second forceps arm 16 may move close to or away from the working end 22 of the first forceps arm 17 along the elongated slot 18.

Since the first forceps arm 17 and the second forceps arm 16 are hinged to each other, when the second forceps arm 16 is rotated relative to the first forceps arm 17, the working end 2 of the second forceps arm 16 performs circumferential motion around a hinge point of the two forceps arms. Therefore, the working end 2 of the second forceps arm 16 may move close to or away from the working end 22 of the first forceps arm 17 along the elongated slot 18.

An inner rod 5 is received in the outer sleeve 1, and one end of the inner rod 5 (i.e., the left end shown in FIG. 9) is connected to the working end 2 of the second forceps arm 16 (i.e., one end of the inner rod 5 extends into the elongated slot 18 from a cavity of the outer sleeve 1 to be connected to the working end 2 of the second forceps arm 16). When the working end 2 of the second forceps arm 16 moves close to or away from the working end 22 of the first forceps arm 17 along the elongated slot 18, the inner rod 5 slides inside the outer sleeve 1. The other end of the inner rod 5 (i.e., the right end shown in FIG. 9) extends outside the outer sleeve 1, and the other end of the inner rod 5 is provided with a distraction ball 6. As shown in FIG. 11, when the working end 2 of the second forceps arm 16 moves close to the working end 22 of the first forceps arm 17 along the elongated slot 18, under the driving of the working end 2 of the second forceps arm 16, the inner rod 5 slides towards the inside of the outer sleeve 1, i.e., sliding towards the left side as shown in FIG. 11. As shown in FIG. 12, when the working end 2 of the second forceps arm 16 moves away from the working end 22 of the first forceps arm 17 along the elongated slot 18, under the driving of the working end 2 of the second forceps arm 16, the inner rod 5 slides towards the outside of the outer sleeve 1, i.e., sliding towards the right side as shown in FIG. 12.

Figure 6:
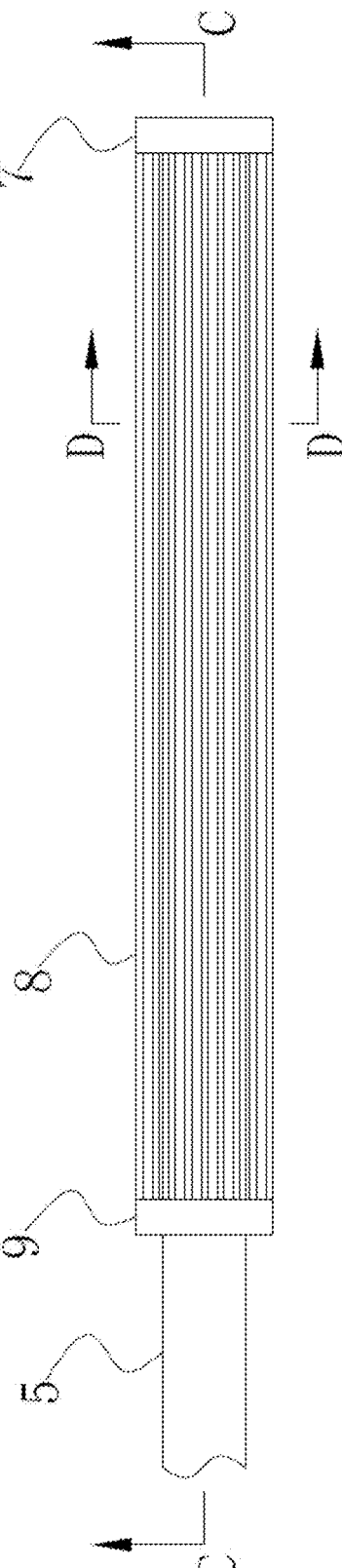
FIG. 6 is a schematic structural diagram of a distraction ball in a contracted state according to the present invention.
Figure 7:
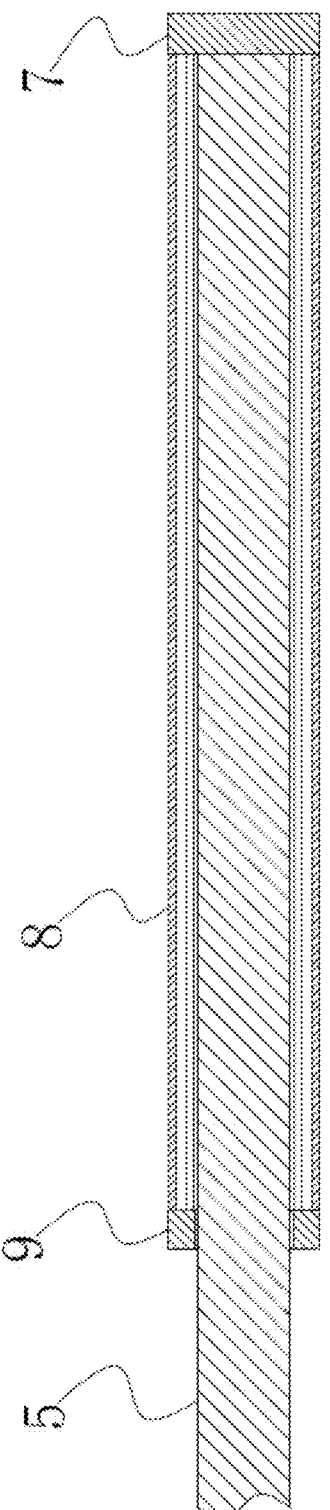
FIG. 7 is a cross-sectional view taken along a line C-C in FIG. 6.
Figure 8:
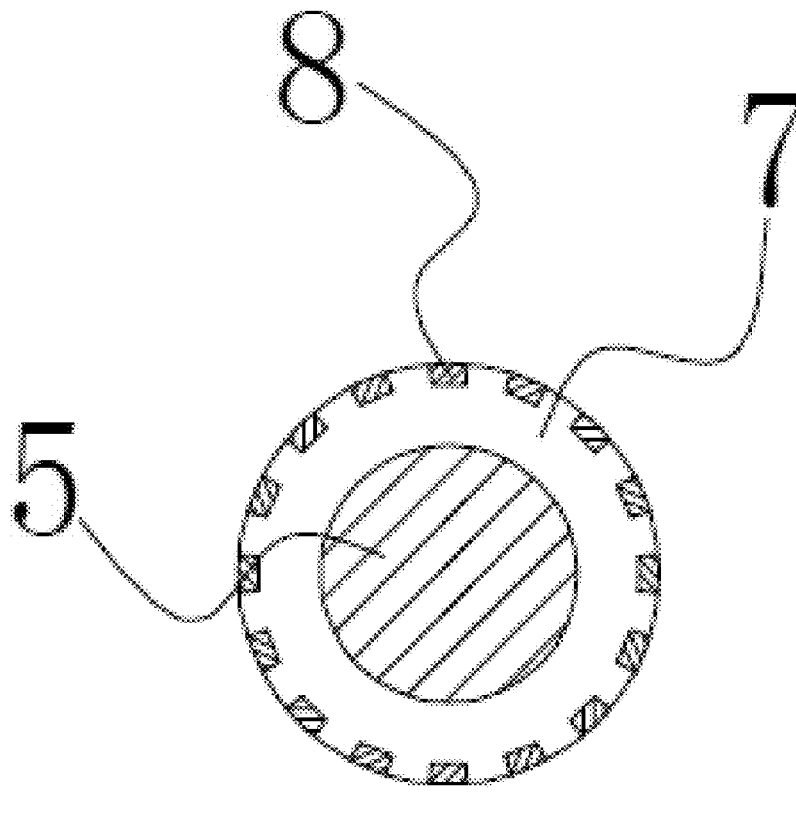
FIG. 8 is a cross-sectional view taken along a line D-D in FIG. 6.

As shown in FIG. 6, in combination with FIG. 7 and FIG. 8, the distraction ball 6 includes a sleeve ring 9, distraction pieces 8, and a stop block 7. The sleeve ring 9 is received on the inner rod 5, and the stop block 7 is fixedly provided on the inner rod 5. The sleeve ring 9 is located between the outer sleeve 1 and the stop block 7. The plurality of distraction pieces 8 are fixedly connected between the sleeve ring 9 and the stop block 7, and the plurality of distraction pieces 8 are arranged circumferentially around the inner rod 5. As shown in FIG. 11 and FIG. 12, when the sleeve ring 9 moves close to the stop block 7, the distraction pieces 8 may be deformed in a protruding manner along a direction away from the inner rod 5. In this case, the distraction ball 6 is in a distracted state.

As shown in FIG. 9, in combination with FIG. 11 and FIG. 12, the working end 2 of the second forceps arm 16 is provided with an elongated opening 11, and the elongated opening 11 is arranged along a length direction of the second forceps arm 16. One end of the inner rod 5 is fixedly provided with a sliding rod 20, and the sliding rod 20 is slidably provided in the elongated opening 11. When the working end 2 of the second forceps arm 16 moves close to or away from the working end 22 of the first forceps arm 17 along the elongated slot 18, the sliding rod 20 slides inside the elongated opening 11. As shown in FIG. 11, when the working end 2 of the second forceps arm 16 moves close to the working end 22 of the first forceps arm 17 along the elongated slot 18, with respect to the second forceps arm 16, the sliding rod 20 slides from the working end 2 of the second forceps arm 16 to the gripping end along the elongated opening 11 (i.e., sliding from top to bottom), and with respect to the outer sleeve 1, the sliding rod 20 moves towards the inside of the outer sleeve 1 (i.e., moving from right to left). Therefore, the sliding rod 20 drives the inner rod 5 to slide towards the inside of the outer sleeve 1. As shown in FIG. 12, when the working end 2 of the second forceps arm 16 moves away from the working end 22 of the first forceps arm 17 along the elongated slot 18, with respect to the second forceps arm 16, the sliding rod 20 slides from the gripping end of the second forceps arm 16 to the working end 2 along the elongated opening 11 (i.e., sliding from bottom to top), and with respect to the outer sleeve 1, the sliding rod 20 moves towards the outside of the outer sleeve 1 (i.e., moving from left to right). Therefore, the sliding rod 20 drives the inner rod 5 to slide towards the outside of the outer sleeve 1.

Figure 2:
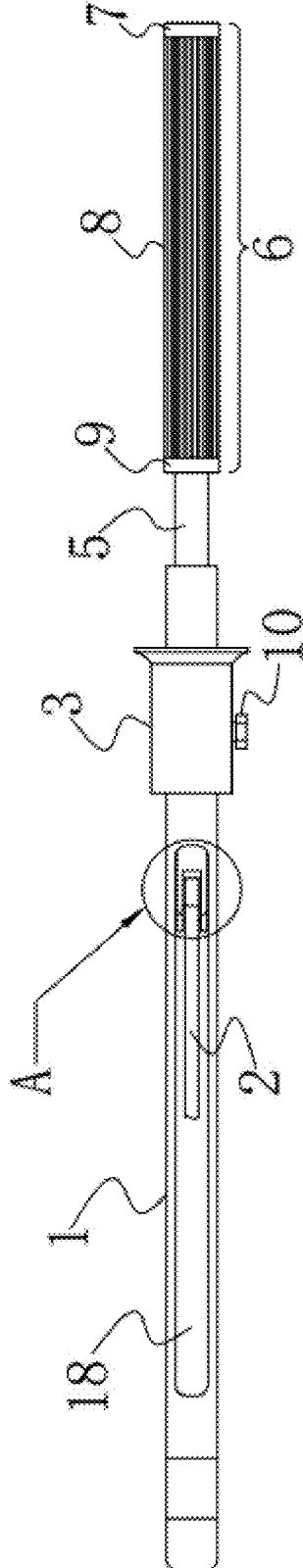
FIG. 2 is a first top view of FIG. 1.
Figure 3:
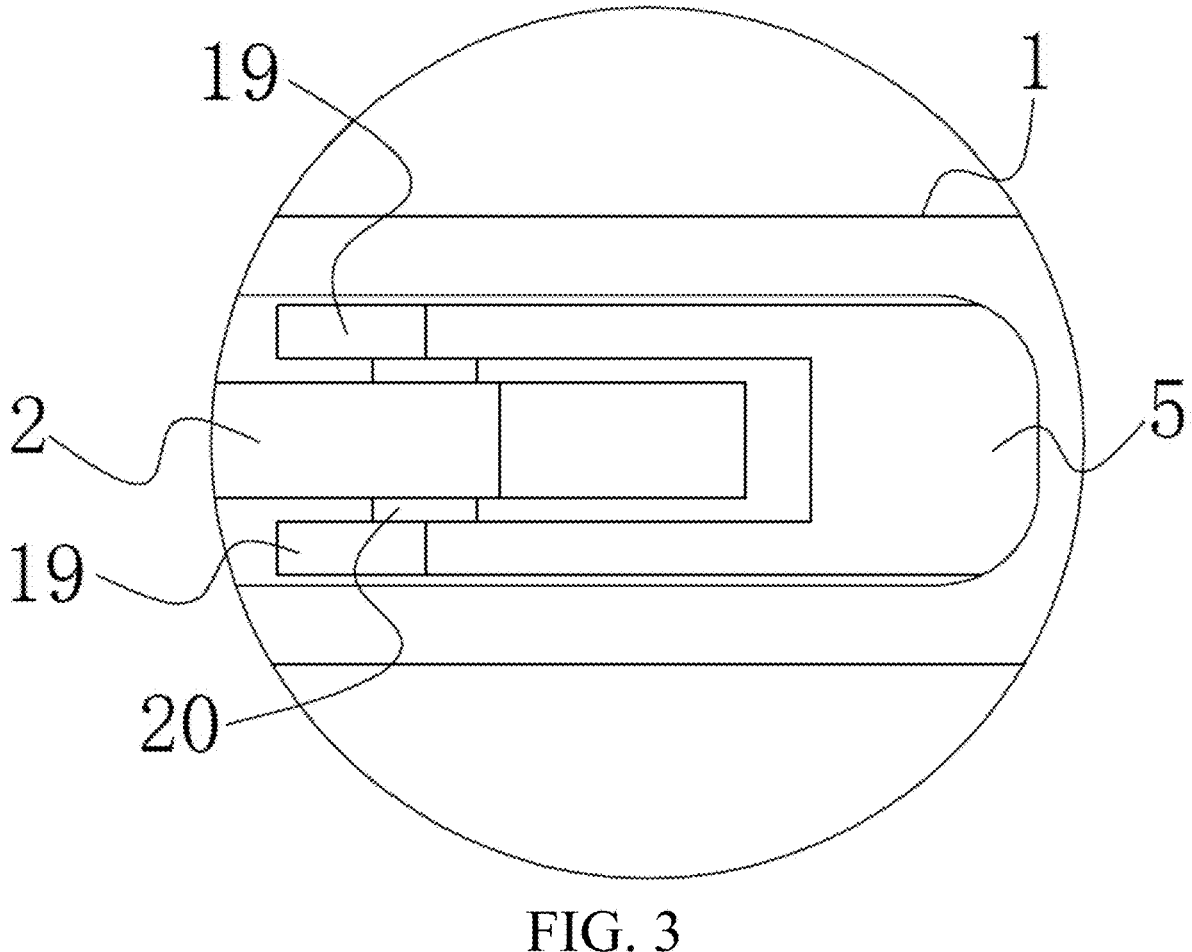
FIG. 3 is a partial enlarged view of a position A in FIG. 2.

As shown in FIG. 2 and FIG. 3, a specific manner in which one end of the inner rod 5 is fixedly provided with the sliding rod 20 is: one end of the inner rod 5 is provided with two support plates 19, and the support plates 19 and the inner rod 5 are integrally formed. The working end 2 of the second forceps arm 16 is located between the two support plates 19. One end of the sliding rod 20 is fixedly connected to one support plate 19, and the other end of the sliding rod 20 passes through the elongated opening 11 to be fixedly connected to the other support plate 19.

Figure 4:
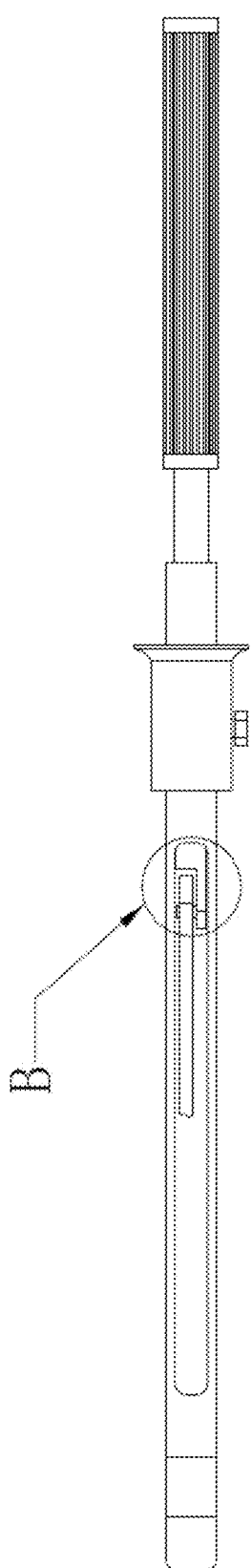
FIG. 4 is a second top view of FIG. 1.
Figure 5:
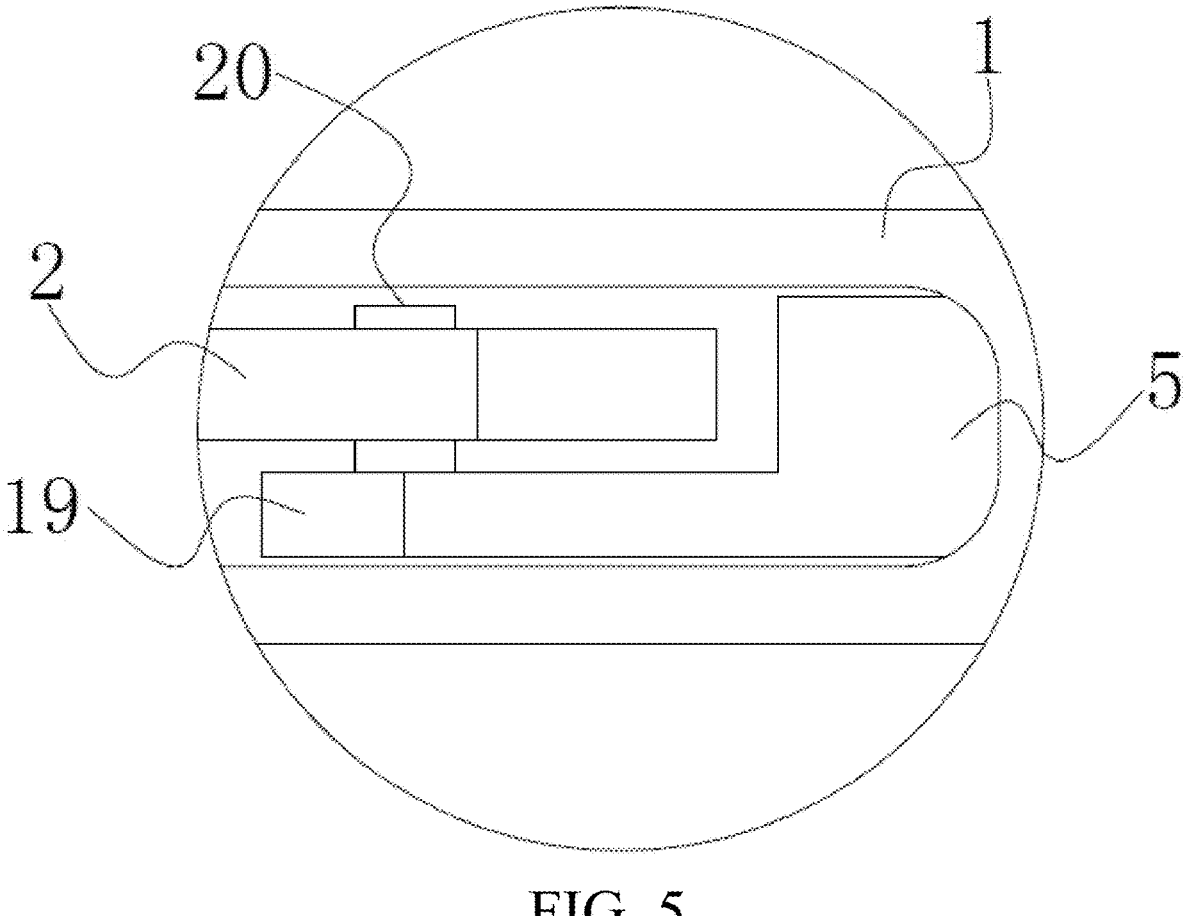
FIG. 5 is a partial enlarged view of a position B in FIG. 4.

Of course, the sliding rod 20 may also be fixed at one end of the inner rod 5 in the following manner: as shown in FIG. 4 and FIG. 5, one end of the inner rod 5 is provided with one support plate 19, the support plate 19 and the inner rod 5 are integrally formed, and the sliding rod 20 is fixedly provided on the support plate 19. The support plate 19 is provided at an edge of one end of the inner rod 5, an accommodation space is formed between the support plate 19 and an end surface of one end of the inner rod 5, and the working end 2 of the second forceps arm 16 is located in the accommodation space. One end of the sliding rod 20 is fixedly connected to the support plate 19, and the other end of the sliding rod 20 is inserted into the elongated opening 11.

As shown in FIG. 1, in combination with FIG. 9, FIG. 11, and FIG. 12, a depth-limiting sleeve 3 is received on the outer sleeve 1, a threaded hole is formed in the wall of the depth-limiting sleeve 3, and a limiting screw 10 is thread-edly connected to the threaded hole. The limiting screw 10 is configured to fix a position of the depth-limiting sleeve 3 on the outer sleeve 1. Scale 4 are arranged on the outer wall of the outer sleeve 1, the scale 4 are arranged along the length direction of the outer sleeve 1, and the scale 4 displays a distance from the distraction ball 6 in a distracted state to the depth-limiting sleeve 3. When the position of the depth-limiting sleeve 3 on the outer sleeve 1 is adjusted, the limiting screw 10 is loosened first, the fixation between the depth-limiting sleeve 3 and the outer sleeve 1 is released, then the depth-limiting sleeve 3 is moved along the outer sleeve 1 to a required position, and then the limiting screw 10 is tightened, so that the limiting screw 10 abuts against the outer sleeve 1, and the depth-limiting sleeve 3 is fixed on the outer sleeve 1.

A first arc-shaped rack 14 is fixedly provided at the gripping end of the first forceps arm 17, and a second arc-shaped rack 15 is fixedly provided at the gripping end of the second forceps arm 16. Both the circle centers of the first arc-shaped rack 14 and the second arc-shaped rack 15 are a hinge point of the first forceps arm 17 and the second forceps arm 16, and the first arc-shaped rack 14 and the second arc-shaped rack 15 are meshed with each other. The functions of the first arc-shaped rack 14 and the second arc-shaped rack 15 are that the first arc-shaped rack 14 and the second arc-shaped rack 15 may be engaged with each other, and when the rotation angle of the second forceps arm 16 relative to the first forceps arm 17 is small, the first arc-shaped rack 14 and the second arc-shaped rack 15 may be meshed with each other, so that the rotation angle of the second forceps arm 16 relative to the first forceps arm 17 may be maintained, thereby facilitating operation of the medical worker. In order to facilitate the operation of the medical worker, the gripping ends of the first forceps arm 17 and the second forceps arm 16 are each provided with a gripping hole 13.

As shown in FIG. 15, before the reducer of the present invention is used, the significant compressed collapsed bony block in the fractured vertebral body 21 is measured by pre-operative CT examination, that is, the distance H from the collapsed bony block to the side surface of the fractured vertebral body 21 is measured. The scale 4 on the outer sleeve 1 is a distance from the distraction ball 6 in the distracted state to the depth-limiting sleeve 3, and is specifically the distance H' from the center of the distraction ball 6 to the right end of the depth-limiting sleeve 3. In order to make the distraction ball 6 just below the collapsed bony block in the distracted state, the position of the depth-limiting sleeve 3 on the outer sleeve 1 is adjusted, and H' is enabled to be equal to H, so that the fractured vertebral body 21 reaches the optimal reduction state.

As shown in FIG. 13 and FIG. 14, when the reducer of the present invention is used, a channel extending into the inside of the fractured vertebral body is provided in a side surface of the fractured vertebral body 21, and the forceps body is operated to insert the distraction ball 6 in a contracted state, the other end of the inner rod 5 and one end of the outer sleeve 1 close to the distraction ball 6 to the channel and push same into the inside of the fractured vertebral body 21 until the right end of the depth-limiting sleeve 3 abuts against the side surface of the fractured vertebral body 21

(the outer diameter of the depth-limiting sleeve 3 is larger than the aperture of the channel, and therefore, the depth-limiting sleeve 3 cannot enter the channel). As shown in FIG. 15, then, the second forceps arm 16 is rotated relative to the first forceps arm 17, so that the working end 2 of the second forceps arm 16 moves close to the working end 22 of the first forceps arm 17 along the elongated slot 18. In this case, the inner rod 5 slides towards the inside of the outer sleeve 1. That is, the distraction ball 6 provided at the other end of the inner rod 5 moves towards the outer sleeve 1 until the sleeve ring 9 of the distraction ball 6 abuts against the outer sleeve 1. As the inner rod 5 continues to slide towards the inside of the outer sleeve 1, the sleeve ring 9 is caused to move close to the stop block 7, so that the distraction pieces 8 may be deformed in a protruding manner along a direction away from the inner rod 5, the distraction ball 6 is in a distracted state, and the distraction ball 6 in the distracted state supports the collapsed bony block of the fractured vertebral body 21. As shown in FIG. 16, next, the second forceps arm 16 is rotated reversely relative to the first forceps arm 17, so that the working end 2 of the second forceps arm 16 moves away from the working end 22 of the first forceps arm 17 along the elongated slot 18. In this case, the inner rod 5 is fixed on the fractured vertebral body 21 due to the fixation effect of the distraction ball 6. Therefore, the outer sleeve 1 slides relative to the inner rod 5 and exits the channel of the fractured vertebral body 21, and after the outer sleeve 1 completely exits the fractured vertebral body 21, it is only required to cut off the inner rod 5 between the outer sleeve 1 and the fractured vertebral body 21, thereby completing reduction of the intermediate collapsed part of the fractured vertebral body 21. Hence, in the present invention, the collapsed bony block may be distracted from the inside of the fractured vertebral body 21, so that the fractured vertebral body 21 is reduced well, and occurrence of long-term complications is reduced.

After the reduction operation is completed, the distraction ball 6 and a part of the inner rod 5 are left in the fractured vertebral body 21, and are no longer removed. Both the distraction ball 6 and the inner rod 5 are made of a titanium alloy. After the distraction ball 6 is distracted, the distraction ball 6 may be maintained in the distracted state. On one hand, the distraction ball 6 is made of a titanium alloy, and after the distraction ball 6 is deformed under the action of external force, if no external force is applied, the shape of the distraction ball 6 cannot be restored; on the other hand, when the distraction ball 6 is in the distracted state, the fractured vertebral body 21 has wrapped the distraction ball 6. As shown in FIG. 16, the left side of the inside of the fractured vertebral body 21 has blocked the distraction pieces 8 so that they cannot move to the left along with the sleeve ring 9 to be received. As long as any one of the foregoing two conditions is satisfied, the distraction ball 6 may be always in the distracted state after being distracted inside the fractured vertebral body 21.

The foregoing embodiments are only for describing the preferred embodiments of the present invention, and are not intended to limit the scope of the present invention. Various modifications and improvements made by persons skilled in the art to the technical solutions of the present invention shall fall within the scopes of protection determined by the claims of the present invention without departing from the design spirit of the present invention.

INDUSTRIAL APPLICABILITY

An intravertebral distraction reducer according to embodiments of the present invention includes a forceps body, an outer sleeve, an inner rod, and a distraction ball, which can distract a collapsed bony block from the inside of a fractured vertebral body, so that the fractured vertebral body is reduced well, and occurrence of long-term complications is reduced. The present invention has good application and promotion value, and can be produced in batches.

The invention claimed is:

1. An intravertebral distraction reducer, comprising a forceps body, wherein the forceps body comprises a first forceps arm and a second forceps arm which are hinged to each other; one end of each of the first forceps arm and the second forceps arm is a gripping end, and the other ends of the first forceps arm and the second forceps arm are working ends;

wherein an outer sleeve is fixedly connected to the working end of the first forceps arm, and an elongated slot is configured to run through the outer sleeve along a radial direction and is also provided along a length direction of the outer sleeve, and the working end of the second forceps arm is inserted into the elongated slot; when the second forceps arm is rotated relative to the first forceps arm, the working end of the second forceps arm moves close to or away from the working end of the first forceps arm along the elongated slot; and an inner rod is received in the outer sleeve, and one end of the inner rod is connected to the working end of the second forceps arm; when the working end of the second forceps arm moves close to or away from the working end of the first forceps arm along the elongated slot, the inner rod slides inside the outer sleeve along a longitudinal direction of the outer sleeve; the other end of the inner rod extends outside the outer sleeve, and the other end of the inner rod is provided with a distraction ball; wherein the distraction ball comprises a sleeve ring, distraction pieces, and a stop block; the sleeve ring is slidably received on the inner rod, and the stop block is fixed on the inner rod; the sleeve ring is located between the outer sleeve and the stop block; the plurality of distraction pieces are fixedly connected between the sleeve ring and the stop block, and the plurality of distraction pieces are arranged circumferentially around the inner rod; and when the sleeve ring moves close to the stop block, the distraction pieces are deformed in a protruding manner along a direction away from the inner rod;

wherein the second forceps arm is rotated relative to the first forceps arm, so that the working end of the second forceps arm moves close to the working end of the first forceps arm along the elongated slot and wherein the inner rod slides towards the inside of the outer sleeve until the sleeve ring of the distraction ball abuts against the outer sleeve and as the inner rod continues to slide towards the inside of the outer sleeve, the sleeve ring is caused to move close to the stop block, so that the distraction ball is in a distracted state, thereby supporting the collapsed fractured vertebral body.

2. The intravertebral distraction reducer according to claim 1, wherein the working end of the second forceps arm is provided with an elongated opening, and the elongated opening is arranged along a length direction of the second forceps arm; one end of the inner rod is fixedly provided with a sliding rod, and the sliding rod is slidably provided in the elongated opening; and when the working end of the second forceps arm moves close to or away from the working end of the first forceps arm along the elongated slot, the sliding rod slides inside the elongated opening.

3. The intravertebral distraction reducer according to claim 2, wherein one end of the inner rod is provided with two support plates, and the support plates and the inner rod are integrally formed; the working end of the second forceps arm is located between the two support plates; and one end of the sliding rod is fixedly connected to one support plate, and the other end of the sliding rod passes through the elongated opening to be fixedly connected to the other support plate.

4. The intravertebral distraction reducer according to claim 3, wherein a depth-limiting sleeve is slidably received on the outer sleeve, a threaded hole is formed in the wall of the depth-limiting sleeve, and a limiting screw is threadedly connected to the threaded hole; the limiting screw is configured to fix a position of the depth-limiting sleeve on the outer sleeve; and a scale is arranged on the outer wall of the outer sleeve, the scale is arranged along the length direction of the outer sleeve, and the scale displays a distance from the distraction ball in a distracted state to the depth-limiting sleeve.

5. The intravertebral distraction reducer according to claim 4, wherein a first arc-shaped rack is fixedly provided at the gripping end of the first forceps arm, and a second arc-shaped rack is fixedly provided at the gripping end of the second forceps arm; and the first arc-shaped rack and the second arc-shaped rack extend along the circumferences of first and second circles having a common center at a hinge connecting the first forceps arm and the second forceps arm, and the first arc-shaped rack and the second arc-shaped rack are meshed with each other.

6. The intravertebral distraction reducer according to claim 5, wherein the gripping ends of the first forceps arm and the second forceps arm are each provided with a gripping hole.

7. The intravertebral distraction reducer according to claim 6, wherein the first forceps arm and the second forceps arm are hinged, wherein the hinge includes a pin shaft.

8. The intravertebral distraction reducer according to claim 7, wherein the elongated slot runs through the central axis of the outer sleeve, and the elongated slot communicates with the cavity of the outer sleeve.

9. The intravertebral distraction reducer according to claim 8, wherein both the distraction ball and the inner rod are made of a titanium alloy.

10. The intravertebral distraction reducer according to claim 2, wherein one end of the inner rod is provided with one support plate, the support plate and the inner rod are integrally formed, and the sliding rod is fixed to the support plate.

11. The intravertebral distraction reducer according to claim 10, wherein a depth-limiting sleeve is slidably received on the outer sleeve, a threaded hole is formed in the wall of the depth-limiting sleeve, and a limiting screw is threadedly connected to the threaded hole; the limiting screw is configured to fix a position of the depth-limiting sleeve on the outer sleeve; and a scale are arranged on the outer wall of the outer sleeve, the scale are arranged along the length direction of the outer sleeve, and the scale displays a distance from the distraction ball in a distracted state to the depth-limiting sleeve.

12. The intravertebral distraction reducer according to claim 11, wherein a first arc-shaped rack is fixedly provided at the gripping end of the first forceps arm, and a second arc-shaped rack is fixedly provided at the gripping end of the second forceps arm; and the first arc-shaped rack and the second arc-shaped rack extend along the circumferences of first and second circles having a common center at a hinge connecting the first forceps arm and the second forceps arm, and the first arc-shaped rack and the second arc-shaped rack are meshed with each other.

13. The intravertebral distraction reducer according to claim 12, wherein the gripping ends of the first forceps arm and the second forceps arm are each provided with a gripping hole.

14. The intravertebral distraction reducer according to claim 13, wherein the first forceps arm and the second forceps arm are hinged, wherein the hinge includes a pin shaft.

15. The intravertebral distraction reducer according to claim 14, wherein the elongated slot runs through the central axis of the outer sleeve, and the elongated slot communicates with the cavity of the outer sleeve.

16. The intravertebral distraction reducer according to claim 15, wherein both the distraction ball and the inner rod are made of a titanium alloy.

\*    \*    \*    \*    \*